(12) United States Patent
Kraetschmer et al.

(10) Patent No.: US 7,697,986 B2
(45) Date of Patent: Apr. 13, 2010

(54) CARDIAC PACEMAKER

(75) Inventors: Hannes Kraetschmer, West Linn, OR (US); Xin Good, Tigard, OR (US)

(73) Assignee: Biotronik CRM Patent AG, Baar (CH)

( * ) Notice: Subject to any disclaimer, the term of this patent is extended or adjusted under 35 U.S.C. 154(b) by 759 days.

(21) Appl. No.: 11/484,336

(22) Filed: Jul. 10, 2006

(65) Prior Publication Data

US 2008/0009910 A1    Jan. 10, 2008

(51) Int. Cl.
*A61N 1/00* (2006.01)
(52) U.S. Cl. ......................................................... 607/9
(58) Field of Classification Search .................. 607/9, 607/14, 17, 16, 27; 600/509, 510
See application file for complete search history.

(56) References Cited

U.S. PATENT DOCUMENTS

| | | | |
|---|---|---|---|
| 3,661,158 A * | 5/1972 | Berkovits ...................... | 607/9 |
| 4,856,523 A | 8/1989 | Sholder et al. | |
| 5,237,992 A | 8/1993 | Poore | |
| 5,374,281 A | 12/1994 | Kristall et al. | |
| 5,417,714 A * | 5/1995 | Levine et al. .................. | 607/9 |
| 6,792,307 B1 * | 9/2004 | Levine et al. .................. | 607/9 |
| 6,871,097 B1 * | 3/2005 | Strandberg .................... | 607/25 |
| 2004/0143299 A1 | 7/2004 | Casavant | |
| 2005/0267538 A1 | 12/2005 | Kramer et al. | |
| 2007/0213777 A1 * | 9/2007 | Betzold et al. ................. | 607/9 |

OTHER PUBLICATIONS

European Search Report, dated Oct. 19, 2007.

* cited by examiner

*Primary Examiner*—George Manuel
*Assistant Examiner*—Robert N Wieland
(74) *Attorney, Agent, or Firm*—Joseph J. Mayo

(57) ABSTRACT

Cardiac pacemaker, having at least one stimulation pulse generator to selectively generate stimulation pulses for delivery to an atrium or to an atrium and a ventricle of a heart in DDD mode, at least one sensing stage adapted to process electrical signals sensed by an atrial and ventricular sensing electrode to detect an atrial or ventricular event and to generate an atrial or ventricular sense signal upon event detection, a control unit connected to the generator and sensing stage and being adapted to trigger the generator in DDD mode, wherein the control unit is adapted to verify proper atrioventricular conduction and to switch from a regular (DDD) mode, wherein scheduled ventricular stimulation pulses having predetermined positive intensity is triggered unless inhibited to a ventricular pulse suppression mode ($V_PS$ mode) wherein no ventricular stimulation pulses or ventricular stimulation pulses of sub-threshold intensity are generated as long as proper atrioventricular conduction is verified.

19 Claims, 3 Drawing Sheets

CARDIAC PACEMAKER

BACKGROUND OF THE INVENTION

1. Field of the Invention

This invention relates generally to the design of cardiac pacemakers and more particularly to dual chamber AV sequential or atrium-synchronous pacemaker.

2. Description of the Related Art

Cardiac pacemakers are medical devices, usually implantable, that can be connected to or that are permanently connected to electrode leads for delivery of electrical stimulations pulses to the tissue (myocardium) of a human heart. Dual chamber pacemakers are capable of generating stimulation pulses for the atrium and the ventricle of a human heart. Biventricular pacemakers usually are capable to stimulate at least three chambers of a human heart that is the right atrium, the right ventricle and the left ventricle.

In a dual chamber pacemaker, this is usually realized by placing electrodes in both the right atrium and right ventricle of the heart.

In a demand-type pacemaker these electrodes are coupled through intravenous and/or epicardial leads to sense amplifiers housed in an implanted pacemaker. Electrical activity occurring in these chambers can thus be sensed. When electrical activity is sensed, the pacemaker assumes that a depolarization following a contraction of the indicated chamber has occurred. If no electrical activity is sensed within a prescribed time interval, typically referred to as an atrial or ventricular escape interval, then a pulse generator, also housed within the pacemaker housing, generates a stimulation pulse that is delivered to the indicated chamber, usually via the same lead as is used for sensing.

Separate stimulation pulse generators are usually provided for each heart chamber (atrium or ventricle) to be stimulated. A control unit triggers the generation of a respective atrial or ventricular stimulation pulse according to a pre-programmed, variable timing regime in order to provide for adequate timing of the stimulation pulses.

A stimulation pulse to the myocardium may cause a contraction of a respective heart chamber, if the myocardium of that chamber is not in a refractory state and if the stimulation pulse intensity is above the stimulation threshold of the myocardium. A sub-threshold stimulation pulse will not cause a cardiac contraction even if delivered to the myocardium in its non-refractory state.

Depending on the mode of operation, a pacemaker only delivers a stimulation pulse (pacing pulse) to a heart chamber (atrium or ventricle) if needed, that is, if no natural excitation of that chamber occurs. Such mode of operation is called an inhibited or demand mode of operation since the delivery of a stimulation pulse is inhibited if a natural excitation of the heart chamber is sensed within a predetermined time interval (usually called escape interval) so the heart chamber is only stimulated if demanded.

In a demand mode, the pacemakers monitors the heart chamber to be stimulated in order to determine if a cardiac excitation (heartbeat) has naturally occurred. Such natural (non-stimulated) excitation, also referred to as "intrinsic" or "signs" cardiac activity, are manifested by the occurrence of recognizable electrical signals that accompany the depolarization or excitation of a cardiac muscle tissue (myocardium). The depolarization of the myocardium is usually immediately followed by a cardiac contraction. For the purpose of the present application, depolarization and contraction may be considered as simultaneous events and the terms "depolarization" and "contraction" are used herein as synonyms.

In order to monitor the heart chamber and thus to determine whether or not a natural contraction of a heart chamber has occurred a pacemaker has a sensing stage during which operation of the pacemaker is connected to an electrode placed in a respective heart chamber. A natural contraction of a heart chamber can be detected by evaluating electrical potentials sensed by this sensing electrode. In the sensed electrical signal the depolarization of an atrium muscle tissue is manifested by occurrence of a signal known as "P-wave". Similarly, the depolarization of ventricular muscle tissue is manifested by the occurrence of a signal known as "R-wave". A P-wave or a R-wave represent an atrial event or a ventricular event, respectively, in the further course of this application.

In a demand mode of operation, the pacemaker monitors the heart for the occurrence of P-waves and/or R-waves. If such signals are sensed within a prescribed time period or time window, which is called atrial or ventricular escape interval, respectively, then the escape interval is reset (i.e., restarted) and generation of a stimulation pulse is inhibited and no unnecessary stimulation pulse is triggered. The escape interval is measured from the last heartbeat, i.e., from the last occurrence of an intrinsic (sensed) atrial event (P-wave, A-sense, AS) if the atrium is monitored, or an intrinsic (sensed) ventricular event (R-wave, V-sense, VS) if the ventricle is monitored, or the generation of a stimulation pulse (V-pace, VP; A-pace, AP) if no respective intrinsic event has occurred. If the escape interval "times-out", i.e., if a time period equal to the escape interval has elapsed without the sensing of a P-wave and/or R-wave (depending upon which chamber of the heart is being monitored), then a stimulation pulse is generated at the conclusion of the escape interval, and the escape interval is reset, i.e., restarted. In this way, the pacemaker provides stimulation pulses "on demand," i.e., only as needed, when intrinsic cardiac activity does not occur within the prescribed escape interval.

Several modes of operation are available in a state of the art multi mode pacemaker. The pacing modes of a pacemaker, both single and dual or more chamber pacemakers, are classified by type according to a three letter code. In such code, the first letter identifies the chamber of the heart that is paced (i.e., that chamber where a stimulation pulse is delivered), with a "V" indicating the ventricle, an "A" indicating the atrium, and a "D" indicating both the atrium and ventricle. The second letter of the code identifies the chamber wherein cardiac activity is sensed, using the same letters, and wherein an "O" indicates no sensing occurs. The third letter of the code identifies the action or response that is taken by the pacemaker. In general, three types of action or responses are recognized: (1) an Inhibiting ("I") response wherein a stimulation pulse is delivered to the designated chamber at the conclusion of the appropriate escape interval unless cardiac activity is sensed during the escape interval, in which case the stimulation pulse is inhibited; (2) a Trigger ("T") response wherein a stimulation pulse to a prescribed chamber of the heart a prescribed period of time after a sensed event; or (3) a Dual ("D") response wherein both the Inhibiting mode and Trigger mode may be evoked, e.g., with the "inhibiting" occurring in one chamber of the heart and the "triggering" in the other.

To such three letter code, a fourth letter "R" may be added to designate a rate-responsive pacemaker and/or whether the rate-responsive features of such a rate-responsive pacemaker are enabled ("O" typically being used to designate that rate-responsive operation has been disabled). A rate-responsive pacemaker is one wherein a specified parameter or combination of parameters, such as physical activity, the amount of oxygen in the blood, the temperature of the blood, etc., is sensed with an appropriate sensor and is used as a physiological indicator of what the pacing rate should be. When enabled, such rate-responsive pacemaker thus provides stimulation pulses that best meet the physiological demands of the patient.

Multiple-mode, demand-type, cardiac pacemakers allow a sequence of contractions of the heart's chamber which equals as far as possible a natural behavior of the healthy heart for damaged or diseased hearts that are unable to do so on their own.

In a healthy heart, initiation of the cardiac cycle normally begins with depolarization of the sinoatrial (SA) node. This specialized structure is located in the upper portion of the right atrium wall and acts as a natural "pacemaker" of the heart. In a normal cardiac cycle and in response to the initiating SA depolarization, the atrium contracts and forces the blood that has accumulated therein into the ventricle. The natural stimulus causing the atrium to contract is conducted to ventricle via the atrioventricular node (AV node) with a short, natural delay, the atrioventricular delay (AV-delay). Thus a short time after an atrial contraction (a time sufficient to allow the bulk of the blood in the atrium to flow through the one-way valve into the ventricle), the ventricle contracts, forcing the blood out of the ventricle to body tissue. A typical time interval between contraction of the atrium and contraction of the ventricle might be 180 ms; a typical time interval between contraction of the ventricle and the next contraction of the atrium might be 800 ms. Thus, in a healthy heart providing proper AV-synchrony an atrial contraction (A) is followed a relatively short time thereafter by a ventricle contraction (V), that in turn is followed a relatively long time thereafter by the next atrial contraction and so on. Where AV synchrony exists, the heart functions very efficiently as a pump in delivering life-sustaining blood to body tissue; where AV synchrony is absent, the heart functions as an inefficient pump.

To mimic the natural behavior of a heart, a dual-chamber pacemaker, in conventional manner, defines a basic atrial escape interval (AEI) that sets the time interval for scheduling an atrial stimulation pulse. The atrial escape interval can be started by a ventricular event and end with an atrial event. A basic AV delay (AVD) or ventricular escape interval (VEI) sets the time interval or delay between an atrial event and a ventricular event. In such embodiment, AEI and AVD (or VEI) thus together define a length of a heart cycle which is reciprocal to the pacing rate at which stimulation pulses are generated and delivered to a patient's heart in the absence of sensed natural cardiac activity.

For the purpose of this application, a "ventricular event" may refer either a natural ventricular excitation (intrinsic ventricular event) which is sensed as an R-wave or a ventricular stimulation pulse (V-pulse, VP). Similarly, an atrial event shall refer to both, a P-wave or an atrial stimulation pulse (A-pulse, AP).

Since the atrial escape interval usually defines the time of delivery of a next scheduled atrial stimulation pulse, and since an atrial stimulation pulse may be timed from the latest ventricular event as well as from the latest atrial event, in some cases the atrial escape interval is an A-A interval.

In general, two kinds of dual-chamber DDD-timing schemes are known:

In atrial-based DDD pacing, all timing is controlled either from the sensing of atrial activity (a P-wave) or an atrial pacing. When a P-wave is sensed, two separate timers are started that operate in parallel. A first timer defines an atrial escape interval, which, if timed-out, results in an atrial paced event. A second timer defines a separate AV delay, which, if timed-out, results in a ventricular paced event. The first and second timers both start upon sensed or paced atrial activity. The AV delay timer does not affect the basic atrial escape interval timer. The atrial escape interval timer thus controls the basic functioning rate of the pacemaker from atrial to atrial event. The ventricle is paced, if needed, at a rate that tracks the sensed atrial rate. If no atrial activity is sensed, then the atrium is also paced at a rate equal to the set rate. Nonetheless, even when operating in such atrial-based mode, there still remains a need to enhance pacemaker longevity, as well as a need to allow the heart to beat at its own rhythm more often.

In atrial based DDD-pacing the atrial escape interval usually is an A-A-interval which is simultaneously started with a ventricular escape interval (AV-interval)

As an alternative to above-described atrial-based DDD pacing, there is also a second type of dual chamber operation known as ventricular-based pacing. In ventricular-based DDD pacing (sometimes referred to as ventricular-based timing), two parallel timers are used, as indicated above. By a ventricular event, a VA Delay timer is started. If the VA Delay timer times-out all the way, an atrial pulse (A-pulse) is provided. Thus, the VA-delay timer defines an atrial escape interval (AEI). If a P-wave is sensed before the VA Delay timer times-out, such sensing terminates the VA Delay timer. The sensing of a P-wave or the generating of an A-pulse thus define a atrial event. A ventricular event also starts a Ventricular Escape Interval timer. If this Ventricular Escape Interval timer times-out all the way, a ventricular pulse (V-pulse) is provided. If an R-wave is sensed before the Ventricular Escape Interval timer times-out, such sensing terminates the Ventricular Escape Interval Timer. The sensing of an R-wave or the generating of a V-pulse thus comprise a ventricular event, which ventricular event again starts both, the VA Delay timer and the Ventricular Escape Interval Timer.

In patients having an AV-block, the natural conduction from the atrium to the ventricle is affected. However, the atrium itself may contract in a natural way with a physiologically adequate rate. In the DDD(R) mode of operation an AV-sequential stimulation or atrium-synchronous pacing is possible, which allows to track intrinsic atrial contractions and to stimulate the ventricle with an (artificial) AV delay after each sensed atrial contraction in order to maintain AV synchronicity. In such mode of operation the maximum AV delay between an atrial event and the next paced ventricular event is given by the ventricular escape interval.

The choice of an adequate duration of an escape interval depends at least on two demands: the escape interval shall reflect the natural timing of a healthy heart. Therefore, the ventricular escape interval would be chosen to match the natural atrioventricular conduction time in a healthy heart. On the other hand, it is an object to allow as many natural contractions of a heart chamber as possible. Therefore, timeout of the escape interval should not occur to early to give the heart the chance to contract on its own.

To meet these demands one of the programmable modes that has been used with programmable pacemakers for many years is a mode known as the "hysteresis" mode. The hysteresis mode is used in conjunction with selected other modes, such as single-chamber demand pacing, to allow the natural sinus rhythm of the heart to persist at rates less than the programmed minimum rate of the pacemaker. The programmed minimum rate of the pacemaker, in turn, sets the atrial escape interval. During pacing, i.e., during those times when the pacemaker is generating stimulation pulses, the pacemaker thus stimulates the heart at the rate set by the atrial escape interval or the sum of the atrial escape interval and the AV delay, respectively, i.e., upon the timing-out of each atrial and/or ventricular escape interval. When the hysteresis mode is enabled, sensed cardiac activity causes the pacemaker escape interval to be extended, or lengthened, thereby providing a longer period of time within which natural cardiac activity may occur before the pacemaker steps in to generate a stimulation pulse. Should the intrinsic rate of the heart fall below the programmed hysteresis rate, i.e., should no intrinsic cardiac activity be sensed during the lengthened escape interval, then a stimulation pulse is generated, and the escape interval reverts back to its initial value, as determined by the programmed minimum rate.

Further intervals set to determine the pacemaker's behavior include refractory periods like a post ventricular refractory period (PVARP), which is started with delivery of a ventricular pacing pulse and during which no atrial activity is sensed thus rendering the pacemaker refractory (insensitive) in the atrium during PVARP. This interval and other intervals will not be discussed further herein since they are known to one skilled in the art.

State of the art pacemakers are disclosed for example in U.S. Pat. No. 4,856,523, U.S. Pat. No. 5,237,992 and U.S. Pat. No. 5,374,281.

It is an object of the present invention to reduce the percentage of ventricular pacing by promoting the intrinsic AV conduction, while maintaining the ability to switch to DDD (R) in the event of unacceptable AV conduction in particular with patients suffering from a sick sinus syndrome (SSS) and AV block I/II.

Dual chamber pacemakers are often implanted in patients with Sick Sinus Syndrome (SSS). Although such patients often have intact AV conduction or 1st degree AV block (AV-block I), the device is often programmed to the DDD(R) mode with factory AV delay setting, which is more suitable to third degree AV block (AV-block III) patients. Therefore, many patients are unnecessarily paced in the ventricle.

There is growing medical evidence that inappropriate ventricular pacing has disadvantageous short-term hemodynamic effects, and may be less than desirable after an extended period of time, e.g. the Mode Selection Trial (MOST) demonstrated that ventricular desynchronization imposed by ventricular pacing even when AV synchrony is preserved increases the risk of heart failure hospitalization and incidence of AF in 2010 SSS patients with normal QRS duration. A 10% increase in cumulative ventricular pacing was associated with a 20% increased risk of CHF hospitalization. This risk increases linearly until cumulative ventricular paced time reached 60% and then plateaus.

BRIEF SUMMARY OF THE INVENTION

The present invention is a pacemaker featuring a ventricular pacing suppression mode of operation in order to reduce the percentage of ventricular pacing in sick sinus syndrome (SSS) and AV block I/II patients by promoting the intrinsic AV conduction, while maintaining the ability to switch to DDD(R) in the event of unacceptable AV conduction. The pacemaker preferably is an implantable pacemaker. The pacemaker has at least one stimulation pulse generator to generate stimulation pulses for delivery to atrium of a human heart or to both, an atrium and a ventricle of the heart in a DDD-mode of operation. The pacemaker also has at least one sensing stage adapted to process electrical signals picked up by an atrial sensing electrode and a ventricular sensing electrode in order to detect an atrial event or a ventricular event and to generate an atrial or a ventricular sense signal upon detection of the atrial event or the ventricular event, respectively. Both, the stimulation pulse generator and the sensing stage are connected to a control unit which is adapted to respond to an output signal of the sensing stage and to trigger the generation of stimulation pulses in a DDD-mode of operation.

The pacemaker according to the invention has the basic features of a DDD(R) pacemaker including ventricular and atrial sensing stages and ventricular and atrial stimulation pulse generators which are operatively connected a control unit providing basic DDD (R) functionality as described above. In addition, the control unit is adapted to verify a proper atrioventricular conduction and to switch from a regular mode of operation such as a DDD mode, wherein scheduled ventricular stimulation pulses having a predetermined intensity are triggered unless inhibited, because a sense signal is received in a predetermined escape interval, to a ventricular pulse suppression mode (VPS mode) of operation. VPS mode occurs when non-effective ventricular stimulation pulses of sub-threshold intensity or ventricular stimulation pulses of zero intensity are triggered at time out of a ventricular escape interval unless the ventricular escape interval is reset and thus delivery of a ventricular stimulation pulse of sub-threshold intensity is inhibited by a ventricular event sensed during the ventricular escape interval.

In a regular mode of operation, regular stimulation pulses of an intensity above capture threshold are generated. Such regular stimulation pulses have an intensity sufficient to cause capture of the myocardium. A sub-threshold stimulation pulse has too low an intensity to cause capture.

Triggering of a stimulation pulse of zero intensity shall mean, that for timing purposes the control unit responds to such stimulation pulse the same way, it would respond to stimulation pulse which has an intensity tailored to cause capture of the myocardium even if no triggering of the stimulation pulse generator needs to occur although it could occur. In other words: triggering of a zero intensity stimulation pulse means that the control unit at least internally generates a trigger signal, which not necessarily is fed forward to the stimulation pulse generator. Thus, triggering of a stimulation pulse of zero intensity results in not generating a stimulation pulse by the stimulation pulse generator although the stimulation pulse is triggered.

The term 'scheduled stimulation pulse' refers to the concept of timing an interval at the end of which a scheduled stimulation pulse shall be delivered unless it is inhibited even if the stimulation pulse generator is not trigged, because the trigger signal is blocked from the stimulation pulse generator, but not inhibited. This means, if proper AV-conduction is determined, the trigger signal is indeed generated but for internal for control purposes only without necessarily leading to an effective stimulation pulse.

In a preferred embodiment, the control unit is adapted to maintain a regular DDD timing (scheduling) of the triggering of stimulation pulses including a ventricular escape interval during operation in the ventricular pulse suppression mode (VPS mode) and to trigger a ventricular stimulation of zero or sub-threshold intensity at the end of the ventricular escape interval if no ventricular sense signal is received during the ventricular escape interval, the ventricular sense signal otherwise is inhibiting the triggering of a ventricular stimulation pulse. Thus, during VPS mode stimulation pulses are scheduled the same as they are scheduled in a regular pacing mode such as DDD and may also be inhibited in a known manner.

In a preferred embodiment of the invention, switching from the regular mode of operation (regular pacing mode) to the VPS mode of operation is controlled by the control unit as follows: while in the regular mode of operation, the control unit initiates Vs searching tests (also known as a Vs search test) at scheduled points of time. Such Vs searching test preferably includes X consecutive heart cycles each of the heart cycles including an AV-delay started with an atrial event. X preferably is a number between 8 and 16, e.g. 10. The AV-delay during a Vs search test is extended with respect to a programmed regular AV-delay. Preferably, the extended AV-delay during Vs searching test has a duration of up to 450 ms. During the Vs searching test the control unit monitors the occurrence of sensed intrinsic ventricular events Vs within the extended AV delay and switches from a regular mode of operation to a VPS mode of operation if one of a set of predetermined conditions referring to the occurrence of ventricular events is met.

These conditions preferably include at least one of the following conditions:
- sensing of a predetermined number (e.g. two) of consecutive Vs events, each Vs event sensed within an extended AV delay during one of a predetermined number of consecutive heart cycles
- sensing of a number of Y intrinsic events Vs in total number of X consecutive cycles Preferably a Vs searching test is initiated at the end of searching intervals, each searching interval being triggered by a preceding Vs searching test. In a preferred embodiment of the pacemaker, the searching intervals are increased each time the Vs searching test has not lead to switching to the VpS(R) mode of operation.

Preferably, the control unit is adapted to perform a switching from the regular mode of pacing to the VpS mode of pacing if an intrinsic ventricular event Vs is sensed within a non-extended, programmed AV delay. Such switching may also occur outside a Vs searching test, that is in between two consecutive searching tests.

In a preferred embodiment of the invention, switching back from the VpS mode of operation to the regular mode of operation is also controlled by the control unit as follows: while in the VpS mode of operation the control unit monitors the occurrence of sensed intrinsic ventricular events and of triggered ventricular stimulation pulses of zero or sub-threshold intensity. The control unit switches from the VPS mode of operation to the regular mode of operation if one of a set of predetermined conditions referring to the occurrence of triggered ventricular stimulation pulses of zero or sub-threshold intensity or of sensed intrinsic ventricular events is met.

Preferably, the set of predetermined conditions for switching from the VpS mode of operation to the regular mode of operation includes at least one of the following conditions:
- occurrence of a predetermined number (e.g. 2) of consecutive triggered ventricular stimulation pulses Vp(0) of zero or sub-threshold intensity within the predetermined number consecutive cycles,
- occurrence of a number of Z triggered ventricular stimulation pulses Vp(0) within a total number of W (e.g. 10) consecutive cycles,
- no sensing of intrinsic ventricular event Vs for a period of time of 1 or more seconds A preferred pacemaker according to the invention provides for a control unit that is adapted to perform an arrhythmia mode switching from an atrium-synchronous mode of pacing to a non-synchronous mode of pacing if a sensed atrial rate exceeds a predetermined atrial rate threshold.

DESCRIPTION OF THE DRAWINGS

The above and other aspects, features and advantages of the present invention will be more apparent from the following more particular description thereof, presented in conjunction with the following drawings wherein.

DETAILED DESCRIPTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
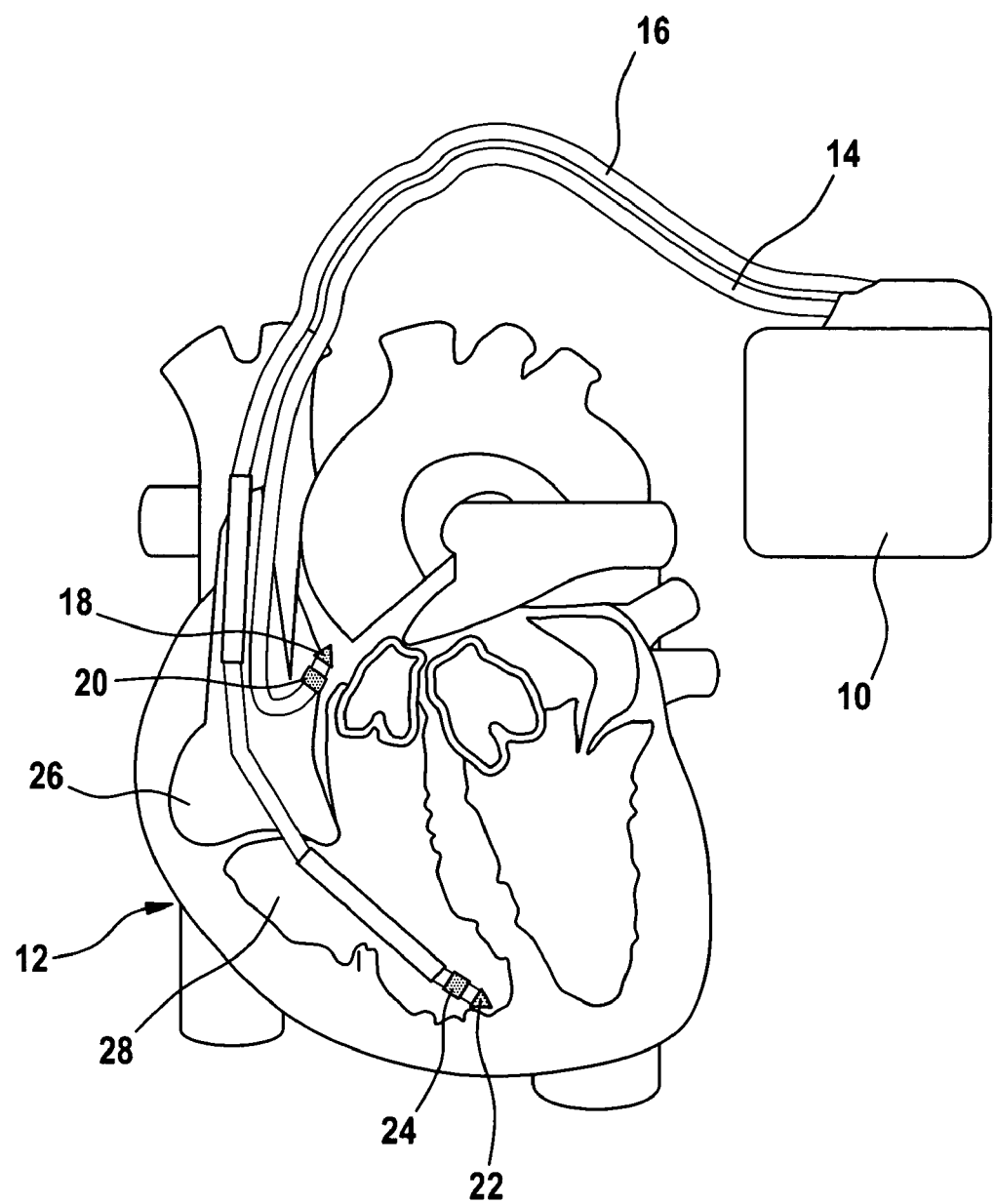
FIG. 1 shows a dual chamber pacemaker connected to pacing/sensing leads placed in a heart

Referring to FIG. 1 a dual chamber pacemaker 10 connected to pacing/sensing leads placed in a heart 12 is illustrated. The pacemaker 10 is coupled to a heart 12 by way of leads 14 and 16, the lead 14 having a pair of right atrial electrodes 18 and 20 that are in contact with the right atria 26 of the heart 12, and the lead 16 having a pair of electrodes 22 and 24 that are in contact with the right ventricle 28 of heart 12. The electrodes 18 and 22 are tip-electrodes at the very distal end of leads 14 and 16, respectively. Electrode 18 is a right atrial tip electrode RA-Tip and electrode 22 is a right ventricular tip electrode 22. Electrodes 20 and 24 are designed as ring electrode in close proximity but electrically isolated from the respective tip electrodes 18 and 22. Electrode 20 forms a right atrial tip electrode RA-Ring und electrode 24 forms a right ventricular ring electrode RV-Ring.

Figure 2:
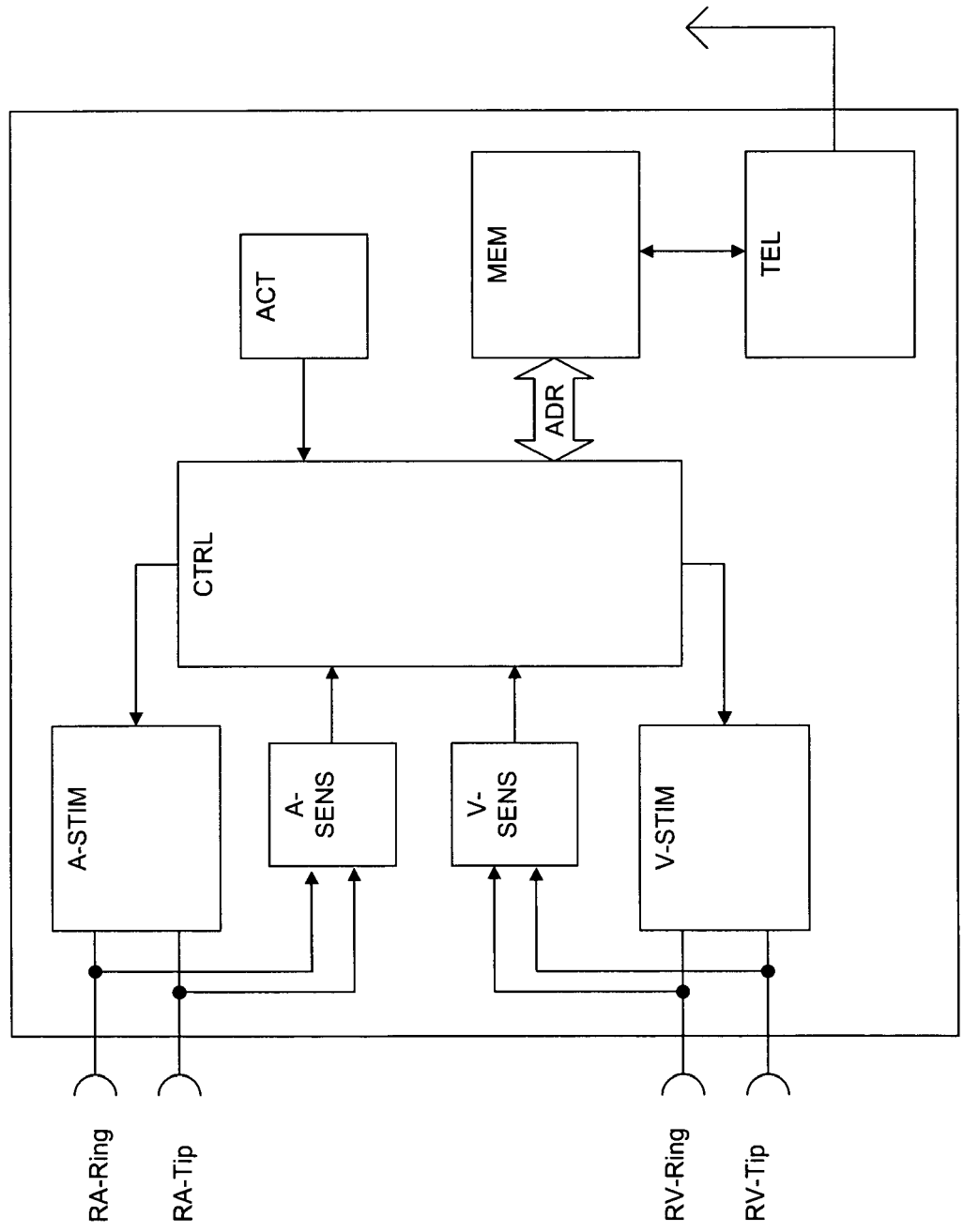
FIG. 2 shows a block diagram of a rate-responsive pacemaker

Referring to FIG. 2 a simplified block diagram of a dual chamber pacemaker 10 is illustrated. During operation leads 14 and 16 are connected to respective output/input terminals of pacemaker 10 as indicated in FIG. 1 and carry stimulating pulses to the tip electrodes 18 and 22 from an atrial stimulation pulse generator A-STIM and a ventricular pulse generator V-STIM, respectively. Further, electrical signals from the atria are carried from the electrode pair 18 and 20, through the lead 14, to the input terminal of an atrial channel sense amplifier A-SENSE; and electrical signals from the ventricles are carried from the electrode pair 22 and 24, through the lead 16, to the input terminal of a ventricular sense channel amplifier R-SENSE (also known as V-SENSE).

Controlling the dual chamber pacer 10 is a control unit CTRL, which is connected to the sense amplifiers A-SENSE and V-SENSE and to the stimulation pulse generators A-STIM and V-STIM. Control unit CTRL receives the output signals from the atrial sense amplifier A-SENSE and from the ventricular sense amplifier V-SENSE. The output signals of sense amplifiers A-SENSE and V-SENSE are generated each time that a P-wave or an R-wave, respectively, is sensed within the heart 12.

Control unit CTRL also generates trigger signals that are sent to the atrial stimulation pulse generator A-STIM and the ventricular stimulation pulse generator V-STIM, respectively. These trigger signals are generated each time that a stimulation pulse is to be generated by the respective pulse generator A-STIM or V-STIM. The atrial trigger signal is referred to simply as the "A-pulse", and the ventricular trigger signal is referred to as the "V-pulse". During the time that either an A-pulse or V-pulse is being delivered to the heart, the corresponding sense amplifier, A-SENSE and/or R-SENSE, is typically disabled by way of a blanking signal presented to these amplifiers from the control unit CTRL, respectively. This blanking action prevents the sense amplifiers A-SENSE and V-SENSE from becoming saturated from the relatively large stimulation pulses that are present at their input terminals during this time. This blanking action also helps prevent residual electrical signals present in the muscle tissue as a result of the pacer stimulation from being interpreted as P-waves or R-waves.

Still referring to FIG. 2, the pacer 10 may also include a memory circuit MEM that is coupled to the control unit CTRL over a suitable data/address bus ADR. This memory circuit MEM allows certain control parameters, used by the control unit CTRL in controlling the operation of the pacemaker 10, to be programmably stored and modified, as required, in order to customize the pacemaker's operation to suit the needs of a particular patient. Such data includes the basic timing intervals used during operation of the pacemaker. Further, data sensed during the operation of the pacer may be stored in the memory MEM for later retrieval and analysis.

A telemetry circuit TEL is further included in the pacemaker 10. This telemetry circuit TEL is connected to the control unit CTRL by way of a suitable command/data bus. Telemetry circuit TEL allows for wireless data exchange between the pacemaker 10 and some remote programming or analyzing device which can be part of a centralized service center serving multiple pacemakers.

The pacemaker 10 in FIG. 1 is referred to as a dual chamber pacemaker because it interfaces with both the right atrium 26 and the right ventricle 28 of the heart 10. Those portions of the pacemaker 10 that interface with the right atrium, e.g., the lead 14, the P-wave sense amplifier A-SENSE, the atrial stimulation pulse generator A-STIM and corresponding portions of the control unit CTRL, are commonly referred to as the atrial channel. Similarly, those portions of the pacemaker 10 that interface with the right ventricle 28, e.g., the lead 16, the R-wave sense amplifier V-SENSE, the ventricular stimulation pulse generator V-STIM, and corresponding portions of the control unit CTRL, are commonly referred to as the ventricular channel.

In order to allow rate adaptive pacing in a DDDR mode, the pacemaker 10 further includes a physiological sensor ACT that is connected to the control unit CTRL of the pacemaker 10. While this sensor ACT is illustrated in FIG. 2 as being included within the pacemaker 10, it is to be understood that the sensor may also be external to the pacemaker 10, yet still be implanted within or carried by the patient. A common type of sensor is an activity sensor, such as a piezoelectric crystal, mounted to the case of the pacemaker. Other types of physiologic sensors are also known, such as sensors that sense the oxygen content of blood, respiration rate, pH of blood, body motion, and the like. The type of sensor used is not critical to the present invention. Any sensor capable of sensing some physiological parameter relatable to the rate at which the heart should be beating can be used. Such sensors are commonly used with "rate-responsive" pacemakers in order to adjust the rate of the pacemaker in a manner that tracks the physiological needs of the patient.

Now, the operative behavior of the pacemaker according to the invention shall be described. This behavior is achieved by adapting control unit CTRL to behave as described hereinafter.

For the purpose of this disclosure, the following abbreviations and definitions are used:

VpS(R) mode Mode of operation wherein no or sub-threshold ventricular stimulation pulses are triggered such that stimulations pulses are in fact suppressed. The Vp suppression mode encourages intrinsic AV conduction by pacing ventricle at 0 or sub-threshold intensity. R indicates the option of rate adaptation.

Vp-DDD(R) mode regular DDD(R) pacing mode wherein stimulation pulses are triggered which shall lead to capture of the ventricle. This mode of operation provides backup ventricular pacing, when acceptable intrinsic AV conduction is lacking.

Vp(0) Ventricular pacing pulse with 0 volt or sub threshold intensity.

Vs searching test A test that actively searches for V senses by extending AVD up to 450 ms for a number of X (e.g. 10) cycles.

Vs searching interval The number of the ventricular pacing events between two Vs searching tests Pacemaker 10 is adapted to provide continuously beat-to-beat monitoring of patient's AV conduction in order to switch back and forth between Vp-DDD(R) mode of operation and VpS(R) mode of operation. Automatic switching between VpS(R) mode and Vp-DDD(R) mode depends on patient's AV conduction condition. The degree of acceptable AV conduction is user programmable. The pacemaker will provide only atrial pacing—if required—as long as the acceptable AV conduction is present. In the event of unacceptable AV conduction, the pacemaker will switch to DDD(R) to support both chambers.

During Vp Suppression mode the timing scheme of a DDD pacemaker is maintained and the intensity of triggered ventricular stimulation pulses is set to zero. Therefore the Vp Suppression mode can be considered as a sub-mode of a more general DDD mode of operation. Vp Suppression mode is available in the DDD and DDD(R) operation modes of the pacemaker.

The feature of setting the intensity of a ventricular stimulation pulse to zero while still maintaining DDD timing promotes the intrinsic AV conduction by only pacing ventricle when intrinsic AV conduction becomes not acceptable or disappeared.

Depending on the presence or absence of acceptable AV conduction, the pacemaker will be in either one mode, which is called VpS(R) mode and promotes the intrinsic conduction, or in the mode, which is called Vp-DDD(R) mode and which provides effective ventricular pacing.

The pacemaker provides automatic switching capabilities between VpS(R) mode and Vp-DDD(R) mode. The underlying principle of switching between the modes is to make it easy to switch to the VpS(R) mode and hard to switch back to Vp-DDD(R) mode, so that the intrinsic conduction is promoted as much as possible without harming the patient.

In order to switch from VpS(R) mode to Vp-DDD(R) mode, the control unit is adapted to schedule Vs searching tests wherein the control unit extend the AV-delay (AVD, ventricular escape interval) to be longer than the user programmed value and count the numbers of detected intrinsic conduction, when AVD is extended. An intrinsic conduction is detected if an intrinsic ventricular conduction is sensed with in the extended AVD started by an atrial event.

Furthermore, the pacemaker provides an arrhythmia mode switching feature to switch from an atrium synchronous mode of pacing such as DDD to an asynchronous pacing mode such as DDI (R) to protect the patient from high ventricular rates. Such arrhythmia mode switching is known as such and is independent of the prevailing mode of operation of the pacemaker, i.e. VpS(R) mode and Vp-DDD(R) mode.

When the Vp Suppression mode is enabled but not yet activated, the device starts in the Vp-DDD(R) mode and looks for intrinsic conduction by starting a Vs searching test at the end of the initial searching interval. Following any suspension, the Vp Suppression feature will resume the Vp-DDD(R) mode.

The switching criteria for switching between VpS(R) mode and Vp-DDD(R) mode are user programmable via the telemetric circuit TEL in order to make the algorithm more or less aggressive in supporting intrinsic conduction.

The pacemaker collects statistical data to provide information about effectiveness of the VpS(R) mode feature, and if the present switching criteria are set appropriate for that specific patient.

Now, the modes of operation of the pacemaker shall be illustrated in more detail:

VpS(R) Mode

In VpS(R) mode the intrinsic AV conduction will be promoted and ventricular pacing with 0 or sub-threshold intensity will be delivered, thus no effective ventricular pacing occurs. The intrinsic conduction is monitored and evaluated on a beat-to-beat basis in the time frame of 450 ms after each used atrial event independent of the rate.

The VpS(R) mode will provide DDD(R) mode timing although only non-effective ventricular pacing with 0 or sub-threshold intensity will be delivered at the end of the programmed AV delay. The obvious behavior reflects the behavior of an ADI(R) mode, with the only difference that a normal DDD(R) timing is still available. This behavior will be realized by having the complete DDD(R) mode timing including a ventricular pacing interrupt available, but not delivering the ventricular pace to the heart.

In the VpS(R) mode, the pacemaker monitors the AV conduction by looking for intrinsic ventricular events up to 450 ms after the preceding atrial event. The pacemaker monitors AV conduction beat-to-beat, and remains in VpS(R) mode as long as there is ventricular sense event within up to 450 ms after the preceding atrial event. If that is not the case a ventricular pace with 0 intensity (Vp(0):no energy but interrupt) is delivered after the up to 450 ms. The pacemaker will switch to Vp-DDD(R) upon detection of one of the following conditions:

occurrence of a predetermined number (e.g. 2) of consecutive triggered ventricular stimulation pulses Vp(0) of zero or sub-threshold intensity within the predetermined number consecutive cycles, a number of Z triggered ventricular Stimulation pulses Vp(0) with zero or sub threshold intensity within a total number of W (e.g. 10) consecutive events, no sensed intrinsic ventricular event Vs for one or more seconds As soon as one of these conditions is met the pacemaker switches to the Vp-DDD(R) mode in order to support the heart with ventricular pacing when there is no acceptable AV conduction or none at all.

Vp-DDD(R) Mode

After programming Vp Suppression to "On", the pacemaker will start in the Vp-DDD(R) mode and look for Vs events. As long as the pacemaker is in that mode, the pacemaker shall operate in the user programmed DDD(R) mode with two exceptions.

One of the two exceptions is that the pacemaker evaluates the patient's intrinsic AV conduction by scheduling Vs searching tests. These Vs searching tests are described below in more detail. As soon as the one of the following conditions is met, the pacemaker shall switch from Vp-DDD(R) mode to VpS(R) mode (more details are provided in the section talking about Vs searching tests):

sensing of a predetermined number of consecutive Vs events, each Vs event sensed within an extended AV delay during one of the predetermined number of consecutive heart cycles a number of Y sensed intrinsic ventricular events Vs within a total number of X (e.g. 10) consecutive cycles A used Vs event is a sensed ventricular event within the regular programmed AV-delay.

The second exception is that the device switches from Vp-DDD(R) mode to VpS(R) mode, if one used Vs event was detected in between two consecutive Vs searching tests. In the case, that you get Vs events within the programmed AV delay (ventricular escape interval) values, the pacemaker shall not wait until the next Vs searching test is carried out in order to switch to the VpS(R) mode since the next Vs searching test may only be scheduled in a few hours.

In times the patient has an unstable AV conduction the pacemaker could switch between the two modes very frequently. This could cause some discomfort for the patient. Therefore, this frequent switching will be limited by implementing a limiting number of 'Maximal switches to Vp-DDD (R) mode per hour'. Whenever this limiting number is reached, Vp Suppression feature (enablement of the VpS(R) mode) shall be suspended until midnight. This number of 'Maximal switches to Vp-DDD(R) mode per hour' does not include switches to Vp-DDD(R) that arise from coming out of arrhythmia mode switches, or enabling the feature at follow-up.

Vs Searching Test

When performing the Vs searching test the pacemaker looks for ventricular sense events Vs within up to 450 ms after the preceding used atrial event. This test will be performed only in the Vp-DDD(R) mode of operation. As mentioned, in the Vp-DDD(R) mode the AV delay will be as programmed by the physician. Only during the searching tests the AV delay will be extended up to 450 ms independent of the rate.

Starting in the Vp-DDD(R) mode, the first Vs searching test will be performed after 180 cycles (Vp-Vp intervals). The pacemaker stays a maximum of X (e.g. 10) beats in the Vs searching test and looks for Vs. As soon as one of the two following conditions is met the feature switches to the VpS (R) mode:

sensing of a predetermined number of consecutive Vs events, each Vs event sensed within an extended AV delay during one of a predetermined number of consecutive heart cycles.

a number of Y sensed intrinsic ventricular events Vs within a total number of X (e.g. 10) consecutive cycles.

Between the Vs searching tests when the pacemaker is in the Vp-DDD(R) mode and uses user programmed AV delay, a single used Vs will cause switching to the VpS(R) mode.

In the case that none of the conditions is met the pacemaker stays in the Vp-DDD(R) mode and goes back to the user programmed AV delay. Each time the Vs searching test has not lead to switching to the VpS(R) mode of operation the searching interval (that is the number of cycles until the next Vs searching test is started) is increased until a 'Maximum Vs searching interval' is reached. This happens by doubling the previous interval. If due to any reason a switch to the VpS(R) mode occurs, the Vs searching interval is reset to 180 cycles. So the pacemaker can search for Vs very quickly again, once you switched back to Vp-DDD(R) mode.

If none of the switching conditions is met until the 'Maximum Vs searching interval' is reached, and no single Vs in between the searches is detected, the Vs searching interval is increased to 20 h. As soon as one of the conditions is met during the Vs searching test or a single used Vs occurs in between two Vs searching tests the pacemaker switches to the VpS(R) mode. Otherwise the pacemaker initiates a Vs searching test every 20 h, and it never becomes disabled. The interval of 20 h was chosen to avoid Vs searching at the fixed time of the day. If there are no Vs events at all, the Vs searching test algorithm does search at a maximum of every 20 h for X (e.g. 10) beats.

Arrhythmia Mode Switch

When the Vp suppression mode is programmed on, an additional arrhythmia mode switch feature is programmed to on, too. Sick Sinus Syndrome patients tent to have sinus tachycardias, which may be conducted to the ventricle. Therefore independent of whether the pacemaker is in the regular mode of operation or in the VpS mode of operation, the arrhythmia mode switch functionality will be available.

Arrhythmia mode switching from an atrium synchronous pacing mode like DDD to a non-synchronous pacing mode like DDI shall prevent the pacemaker from tracking atrial events at to high a rate and to pace the ventricle with that high rate. Therefore, the pacemaker having the arrhythmia mode switch feature implemented will switch to a non-synchronous pacing mode if the rate of sensed atrial events exceeds a predetermined value. Other criteria for arrhythmia mode switching well known in the art may be implemented as well.

Whenever the arrhythmia mode switching criteria is met, the pacemaker shall switch to DDI(R) mode, regardless whether Vp suppression is active or not. The pacemaker stays in that mode until predetermined resynchronization criteria are met. After resynchronization from arrhythmia mode switch, the pacemaker switches to Vp-DDD(R) mode in order to have defined conditions after an episode of tachycardia. The initial Vs searching test will occur after the searching interval. The duration of the searching interval depends on from which mode the pacemaker did mode switch:

In the case the pacemaker did mode switch from the VpS (R) mode to the DDI mode the search interval is set to 180 cycles.

In the case the pacemaker did mode switch from the Vp-DDD(R) mode to the DDI (R) mode, the searching interval stays at the value before the arrhythmia mode switch did occur.

Figure 3:
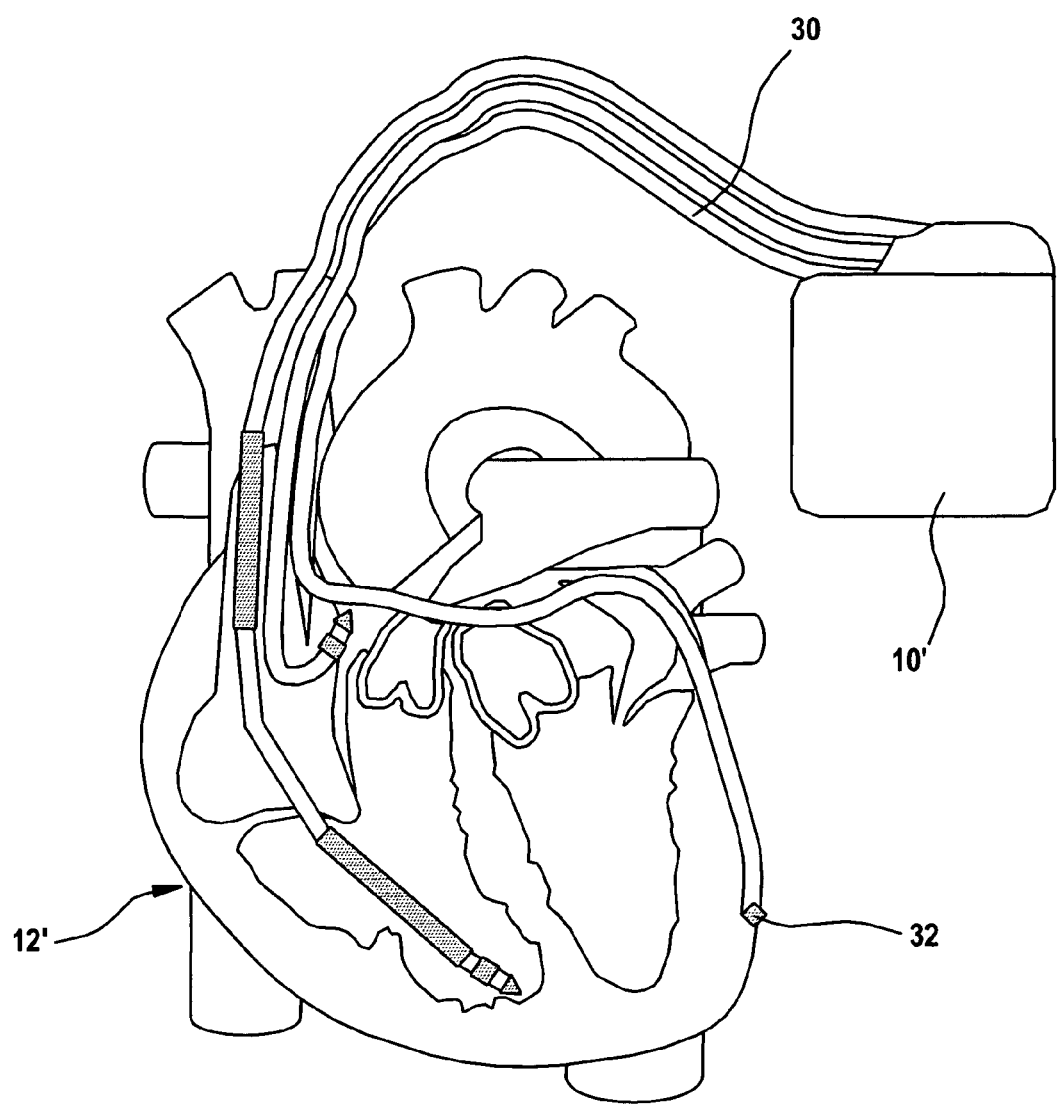
FIG. 3 shows a biventricular three chamber pacemaker connected to pacing/sensing leads placed in a heart

Just for the purpose to indicate, that the concept of triggering suppressed stimulation pulses is applicable to more than one chamber of a heart, FIG. 3 illustrates a three chamber pacemaker 10' featuring an additional left ventricular pacing an sensing channel being connected to a left ventricular electrode lead 30. Electrode lead 30 is implanted via the sinus coronarius of heart 12' and bears a left ventricular tip electrode 32 at its distal end.

Although two exemplary embodiments of the present invention have been shown and described, it should be apparent to those of ordinary skill that a number of changes and modifications to the invention may be made without departing from the spirit and scope of the invention. For example, the concept of triggering suppressed pacing pulses can be applied to three or four chamber pacemakers without departing from the claimed invention. In particular in a biventricular pacemakers as indicated in FIG. 3 left ventricular stimulation pulses can be suppressed depending upon the result of an interventricular conduction test similar to the conduction test disclosed above. This invention can readily be adapted to such devices by following the present teachings. All such changes, modifications and alterations should therefore be recognized as falling within the scope of the present invention.

What is claimed is:

1. A cardiac pacemaker, comprising:
   at least one stimulation pulse generator to selectively generate stimulation pulses for delivery to an atrium of a heart or to said atrium and a ventricle or two ventricles of said heart;
   at least one sensing stage configured to process electrical signals picked up by an atrial sensing electrode or a ventricular sensing electrode in order to detect an atrial event or a ventricular event and to generate at least one sensing stage output signal comprising an atrial or a ventricular sense signal upon detection of said atrial event or said ventricular event, respectively;
   a control unit connected to said at least one stimulation pulse generator and to said at least one sensing stage and wherein said control unit is configured to respond to said at least one sensing stage output signal and to trigger said at least one stimulation pulse generator in a regular mode of operation, wherein a scheduled ventricular stimulation pulse having a predetermined intensity causing capture is triggered unless inhibited;
   wherein said control unit is configured to verify a proper atrioventricular conduction and depending on a presence of acceptable AV conduction to switch from said regular mode of operation, wherein said scheduled ventricular stimulation pulse having said predetermined intensity causing capture is triggered unless inhibited to a ventricular pulse suppression mode of operation wherein no ventricular stimulation pulses or non-effective ventricular stimulation pulses of sub-threshold intensity not causing capture are generated unless inhibited as long as said cardiac pacemaker is in said ventricular pulse suppression mode; and
   wherein said control unit is configured to maintain a regular DDD timing of triggering of said stimulation pulses including a ventricular escape interval while in said ventricular pulse suppression mode of operation and to trigger a ventricular stimulation of zero or sub-threshold intensity following said ventricular escape interval if said ventricular sense signal is not received during said ventricular escape interval, wherein said ventricular sense signal otherwise is inhibiting a triggering of a ventricular stimulation pulse.

2. The cardiac pacemaker according to claim 1, wherein said proper atrioventricular conduction is verified if said ventricular sense signal is received during a ventricular escape interval.

3. The cardiac pacemaker according to claim 2, wherein said regular mode of operation and said ventricular pulse suppression mode of operation are both DDD modes.

4. The cardiac pacemaker according to claim 3, wherein said cardiac pacemaker comprises a physiological sensor connected to said control unit and wherein said regular mode of operation is a rate adaptive pacing mode.

5. The cardiac pacemaker according to claim 3, wherein said cardiac pacemaker comprises a physiological sensor connected to said control unit and wherein said regular mode of operation is a DDDR mode.

6. The cardiac pacemaker according to claim 1 wherein said control unit, while in said regular mode of operation, is configured to perform a Vs search test at scheduled points of time, wherein during said Vs search test an AV-delay is extended with respect to a regular programmed AV delay and said control unit monitors an occurrence of sensed intrinsic ventricular events within said extended AV delay and switches from said regular mode of operation to said ventricular pulse suppression mode of operation if one of a set of predetermined conditions referring to an occurrence of ventricular events is met.

7. The cardiac pacemaker according to claim 6, wherein said Vs search test is configured to monitor a predetermined number of X consecutive heart cycles.

8. The cardiac pacemaker according to claim 6 wherein said set of predetermined conditions for switching from said regular mode of operation to said ventricular pulse suppression mode of operation comprises
   occurrence of a predetermined number of consecutive Vs events, each Vs event sensed within an extended AV delay during one of a predetermined number of consecutive heart cycles, or
   occurrence of Y Vs events in a predetermined total number of consecutive cycles wherein Y is equal or smaller than said predetermined total number.

9. The cardiac pacemaker according to claim 6 wherein said control unit is configured to schedule said Vs search test following search intervals, wherein each search interval is triggered by a preceding Vs search test.

10. The cardiac pacemaker according to claim 9 wherein said search intervals are increased each time said Vs search test has not led to switching to a VpS(R) mode of operation.

11. The cardiac pacemaker according to claim 1 wherein said control unit is configured to perform a switch from said regular mode of operation to said ventricular pulse suppression mode of operation if an intrinsic ventricular event Vs is sensed within a non-extended, programmed AV delay.

12. The cardiac pacemaker according to claim 1 wherein said control unit while in said ventricular pulse suppression mode of operation is configured to monitor an occurrence of sensed intrinsic ventricular events and of triggered ventricular stimulation pulses of zero or sub-threshold intensity and to switch from said ventricular pulse suppression mode of operation to said regular mode of operation if one of a set of predetermined conditions referring to an occurrence of said triggered ventricular stimulation pulses of zero or sub-threshold intensity or of said sensed intrinsic ventricular events is met.

13. The cardiac pacemaker according to claim 12, wherein said set of predetermined conditions for switching from said ventricular pulse suppression mode of operation to a regular mode of operation comprises:
   occurrence of a predetermined number of consecutive triggered ventricular stimulation pulses Vp(0) of zero or sub-threshold intensity within a predetermined number consecutive cycles, or
   occurrence of a number of Z triggered ventricular stimulation pulses Vp(0) within a total number of W consecutive cycles, wherein Z is smaller than W, or
   no occurrence of an intrinsic ventricular event Vs for a period of time of 1 or more seconds.

14. The cardiac pacemaker according to claim 1 wherein said control unit is configured to perform an arrhythmia mode switching from an atrium-synchronous mode of operation to a non-synchronous mode of operation if a sensed atrial rate exceeds a predetermined atrial rate threshold.

15. A cardiac pacemaker, comprising:
   at least one stimulation pulse generator to selectively generate stimulation pulses for delivery to an atrium of a heart or to said atrium and a ventricle or two ventricles of said heart;
   at least one sensing stage configured to process electrical signals picked up by an atrial sensing electrode or a ventricular sensing electrode in order to detect an atrial event or a ventricular event and to generate at least one sensing stage output signal comprising an atrial or a ventricular sense signal upon detection of said atrial event or said ventricular event, respectively;
   a control unit connected to said at least one stimulation pulse generator and to said at least one sensing stage and wherein said control unit is configured to respond to said at least one sensing stage output signal and to trigger said at least one stimulation pulse generator in a regular mode of operation, wherein a scheduled ventricular stimulation pulse having a predetermined intensity causing capture is triggered unless inhibited;
   wherein said control unit is configured to verify a proper atrioventricular conduction and depending on a presence of acceptable AV conduction to switch from said regular mode of operation, wherein said scheduled ventricular stimulation pulse having said predetermined intensity causing capture is triggered unless inhibited to a ventricular pulse suppression mode of operation wherein no ventricular stimulation pulses or non-effective ventricular stimulation pulses of sub-threshold intensity not causing capture are generated unless inhibited as long as said cardiac pacemaker is in said ventricular pulse suppression mode wherein said control unit while in said ventricular pulse suppression mode of operation is configured to monitor an occurrence of sensed intrinsic ventricular events and of triggered ventricular stimulation pulses of zero or sub-threshold intensity and to switch from said ventricular pulse suppression mode of operation to said regular mode of operation if one of a set of predetermined conditions referring to an occurrence of said triggered ventricular stimulation pulses of zero or sub-threshold intensity or of said sensed intrinsic ventricular events is met.

16. The cardiac pacemaker according to claim 15 wherein said control unit, while in said regular mode of operation, is configured to perform a Vs search test at scheduled points of time, wherein during said Vs search test an AV-delay is extended with respect to a regular programmed AV delay and said control unit monitors an occurrence of sensed intrinsic ventricular events within said extended AV delay and switches from said regular mode of operation to said ventricular pulse suppression mode of operation if one of a set of predetermined conditions referring to an occurrence of ventricular events is met.

17. The cardiac pacemaker according to claim 16 wherein said set of predetermined conditions for switching from said regular mode of operation to said ventricular pulse suppression mode of operation comprises
   occurrence of a predetermined number of consecutive Vs events, each Vs event sensed within an extended AV delay during one of a predetermined number of consecutive heart cycles, or
   occurrence of Y Vs events in a predetermined total number of consecutive cycles wherein Y is equal or smaller than said predetermined total number.

18. The cardiac pacemaker according to claim 15 wherein said control unit while in said ventricular pulse suppression mode of operation is configured to monitor an occurrence of sensed intrinsic ventricular events and of triggered ventricular stimulation pulses of zero or sub-threshold intensity and to switch from said ventricular pulse suppression mode of operation to said regular mode of operation if one of a set of predetermined conditions referring to an occurrence of said triggered ventricular stimulation pulses of zero or sub-threshold intensity or of said sensed intrinsic ventricular events is met.

19. The cardiac pacemaker according to claim 18, wherein said set of predetermined conditions for switching from said ventricular pulse suppression mode of operation to a regular mode of operation comprises:
   occurrence of a predetermined number of consecutive triggered ventricular stimulation pulses Vp(0) of zero or sub-threshold intensity within a predetermined number consecutive cycles, or
   occurrence of a number of Z triggered ventricular stimulation pulses Vp(0) within a total number of W consecutive cycles, wherein Z is smaller than W, or
   no occurrence of an intrinsic ventricular event Vs for a period of time of 1 or more seconds.

* * * * *